US005532224A

United States Patent [19]

Desai et al.

[11] Patent Number: 5,532,224
[45] Date of Patent: Jul. 2, 1996

[54] CONTACT LENS CLEANING COMPOSITION CONTAINING POLYALKLENE OXIDE MODIFIED SILOXANES

[75] Inventors: Nayan N. Desai, Freehold, N.J.; Ronald P. Quintana; Masood A. Chowhan, both of Arlington, Tex.

[73] Assignee: Alcon Laboratories, Inc., Fort Worth, Tex.

[21] Appl. No.: 172,625

[22] Filed: Dec. 22, 1993

[51] Int. Cl.[6] .......................... A01N 55/00; A01N 55/08; A61K 31/69

[52] U.S. Cl. ............................ 514/63; 252/351; 252/357; 510/112; 510/115

[58] Field of Search ......................... 514/63; 252/174.15, 252/351, 357

[56] References Cited

U.S. PATENT DOCUMENTS

| | | | |
|---|---|---|---|
| 3,171,752 | 3/1965 | Rankin | 106/194 |
| 3,299,112 | 1/1967 | Bailey | 260/448.2 |
| 3,767,788 | 10/1973 | Rankin | 424/78 |
| 4,025,456 | 5/1977 | Litteral et al. | 252/351 |
| 4,048,122 | 9/1977 | Sibley et al. | 252/541 |
| 4,407,791 | 10/1983 | Stark | 424/80 |
| 4,493,783 | 1/1985 | Su et al. | 252/174.23 |
| 4,525,346 | 6/1985 | Stark | 424/80 |
| 4,808,239 | 2/1989 | Schafer et al. | 134/42 |
| 5,370,816 | 12/1994 | Balzer et al. | 252/174.21 X |

FOREIGN PATENT DOCUMENTS 57-168218 10/1982 Japan .

OTHER PUBLICATIONS

Vick, S. C., "Structure/Property Relationships for Silicone Polyalkyleneoxide Copolymers and Their Effects on Performance in Cosmetics," Soap/Cosmetics/Chemical Specialties, 36ff, May 1984.

Schmidt, G. L. F., "Specific Properties of Silicone Surfactants and Their Applications", In D. R. Karsa (Editor), Industrial Applications of Surfactants, Special Publication No. 59, The Royal Society of Chemistry, Burlington House, London, 1987, pp. 24–32.

"Silicon Compounds: Register and Review," 5th edition, R. Anderson, G. L. Larson and C. Smith, Editors, Hüls America, Inc., Piscataway, New Jersey, 1991, p. 276.

"Silwet Surface Active Copolymers," Union Carbide Corporation, 1985 (brochure).

*Surface Chemistry and Dental Integuments*A. Lasslo and R. P. Quintana, Editors; Charles C. Thomas Publisher; Springfield, Illinois, 1973, pp. 401–404.

Goldschmidt informiert..., Special Issue taken from No. 63–Apr./1984 "Organo–Polysiloxane Copolymers", H.–J. Kollmeier and R. D. Langenhagen.

"Silicon Compounds Register and Review", R. Anderson, B. Arkles, G. L. Larson, Editors, *Petrarch Systems Silanes & Silicones*, 1987, p. 285.

Derwent Abstract of JP 57 168218 (i.e., Reference AL, above), Oct. 1982.

"LC–65® Daily Contact Lens Cleaner", *1993 Physicians'Desk Reference for Ophthalmology*, 21 Edition, C. Weisbecker, et al. Editorial Consultants, Medical Economics Data, Montvale, NJ, 1993, p. 339.

Japan Patent Information Organization Abstract of JP 57–168218 (i.e., Reference AL, above), Oct. 1982.

American Chemical Society Abstract of JP 57–168218 (i.e., Reference AL, above), Oct. 1982.

*Primary Examiner*—Paul F. Shaver
*Attorney, Agent, or Firm*—James A. Arno; Gregg C. Brown

[57] ABSTRACT

Compositions and methods are provided for cleaning and wetting of contact lenses, especially rigid, gas-permeable contact lenses. The compositions comprise low molecular weight polyalkylene oxide modified siloxanes, which are particularly effective in removing lipids from the surface of contact lenses.

21 Claims, No Drawings

CONTACT LENS CLEANING COMPOSITION CONTAINING POLYALKLENE OXIDE MODIFIED SILOXANES

BACKGROUND OF THE INVENTION

The present invention is directed to filling the need for an improved product for removing lipid deposits from contact lenses, particularly RGP lenses, as well as providing compositions which improve the wettability and overall comfort of contact lenses.

The removal of deposits of proteins and other materials from the surfaces of contact lenses has been the subject of extensive research in the contact lens care industry since large scale introduction of contact lenses in the 1960's. Much of the research has focused on the removal of protein deposits from contact lenses. There are today a number of cleaning products on the market which remove protein deposits on contact lenses. Enzyme-containing cleaners are especially effective in this regard. Although other types of soilants on contact lenses have received somewhat less attention than proteins, such deposits can also be quite troublesome to the wearers of contact lenses. This is particularly true of lipid deposits which have become increasingly recognized as a significant problem for wearers of contact lenses, especially the lenses classified as "rigid gas-permeable" or "RGP" lenses. See, e.g., S.W. Huth and H.G. Wagner, "Identification and Removal of Deposits on Polydimethylsiloxane Silicone Elastomer Lenses", International Contact Lens Clinic, 8 (July–August), 19–27, 1981; D.E. Hart, "Contact Lens/Tear Film Interactions: Depositions and Coatings," In O.H. Dabezies, Jr. (Chief Editor), Contact Lenses (The CLAO Guide to Basic Science and Clinical Practice), Second Edition, Volume 2, Little, Brown and Company, Boston, 1988, pp. 45.A–1–45.A–27; R.C. Tripathi and B.J. Tripathi, "Lens Spoilage." In O.H. Dabezies, Jr. (Chief Editor), Contact Lenses (The CLAO Guide to Basic Science and Clinical Practice), Second Edition, Volume 2, Little, Brown and Company, Boston, 1988, pp. 45.1–45.33; R.M. Grohe, "Special Clinical Considerations." In E.S. Bennett and R.M. Grohe (Editors), Rigid Gas-Permeable Contact Lenses, Professional Press Books/Fairchild Publications, New York, 1986. pp. 151–174.

The use of polymeric surfactants in contact lens care products has been described in numerous publications. Reference is made to the following publications for further background concerning such usage:

U.S. Pat. No. 3,171,752 (Rankin), issued Mar. 2, 1965;

U.S. Pat. No. 3,767,788 (Rankin), issued Oct. 23, 1973;

U.S. Pat. No. 4,048,122 (Sibley, et al.), issued Sep. 13, 1977;

U.S. Pat. No. 4,493,783 (Su, et at.), issued Jan. 15, 1985; and

U.S. Pat. No. 4,808,239 (Schafer, et al.), issued Feb. 28, 1989.

In addition, various types of contact lens care products containing surfactants have been marketed in the United States and other countries. Those skilled in the art of contact lens care products will be generally familiar with such products, which include Lobob Daily Cleaner, Lobob Laboratories, San Jose, CA; LC-65, Allergan, Irvine, CA; Titan II, Barnes-Hind Pharmaceuticals, Inc., Sunnyvale, CA; and Opti-Clean®, Alcon Laboratories, Inc., Fort Worth, TX, for example. The above-cited patent issued to Sibley, et al. is believed to relate to the Titan II product, which has been marketed by Barnes-Hind. The patent issued to Su, et al., relates to the Opti-Clean® product.

Notwithstanding such surfactant containing products, there remains a need for improved products capable of achieving even greater cleaning of contact lenses. In view of the significant worldwide market for rigid gas-permeable (RGP) lenses, there is a particular need for products which are more effective in cleaning these lenses. RGP lenses are generally less susceptible to formation of protein deposits than are soft (hydrogel) contact lenses, especially those categorized as ionic, high-water-content lenses. However, RGP lenses are susceptible to formation of lipid deposits. Therefore, the removal of lipid deposits is today a principal focus of research in the area of cleaning products for RGP lenses. The need for a product which effectively removes lipid deposits from these lenses was a principal impetus for the present invention.

A further motivation for the present invention was the need for a product which is generally effective in removing lipid deposits from all types of contact lenses, as well as enhancing the wettability of contact lenses. While other factors also contribute to lens-wear comfort, the wettability of a contact lens (i.e., the ability of the lens to become wetted with tear fluid which normally hydrates and lubricates the cornea upon blinking of the eye) is a critical factor with respect to the comfort of the lens when placed on the cornea. It is therefore highly desirable to treat the surface of contact lenses with a composition that enhances the wettability of the lenses while being worn. This is particularly true with RGP lenses and other types of lenses having a lower water content than soft, hydrogel type lenses.

SUMMARY OF THE INVENTION

The present invention is based on the discovery that certain compounds within the class of surfactants known as "hydrophilic silicones" (which includes compounds referred to as polyalkylene oxide modified siloxanes, polyalkyleneoxide modified polydimethylsiloxanes, dimethylsiloxane-alkylene oxide copolymers, and silicone polyalkyleneoxide copolymers) are extremely effective in cleaning and wetting contact lenses. This class of surfactants is known. Reference is made to the following publications for further information concerning these surfactants: U.S. Pat. Nos. 3,299,112, 4,025,456, and 4,071,483. See, generally, S.C. Vick, "Structure/Property Relationships for Silicone Polyalkyleneoxide Copolymers and Their Effects on Performance in Cosmetics," Soap/Cosmetics/Chemical Specialties, 36ff, May, 1984; and G.L.F. Schmidt, "Specific Properties of Silicone Surfactants", In D.R. Karsa (Editor), Industrial Applications of Surfactants, Special Publication No. 59, The Royal Society of Chemistry, Burlington House, London, 1987, pages 24–32.

Surprisingly, it has been discovered that certain low molecular weight polyalkylene oxide modified siloxanes possess superior cleaning activity. The low molecular weight, polyalkylene oxide modified siloxanes of the present invention include a sufficiently high weight percent of the non-siloxane portion to achieve solubility in water. While the precise mechanism of the cleaning action is not fully understood, these surfactants are believed to remove lipid deposits and other materials from the surfaces of contact lenses by what may be generally described as surface-active displacement of the deposits by the polymeric surfactant.

The compositions and methods of the present invention are considered to have unexpected and significant advantages over prior compositions and methods for cleaning and wetting contact lenses. The superiority of the present compositions in performing both of these functions is a chief advantage. Moreover, the superior cleaning ability of the compositions has practical significance. Many lens wearers are not appropriately diligent or compliant in implementing cleaning procedures recommended by lens care product manufacturers or ophthalmic practitioners. In such instances, the superior cleaning efficacy of the surfactant compositions of the present invention can compensate for less than optimal compliance, providing the lens wearer with a cleaner, more comfortable lens than otherwise would have been obtained.

The present invention entails compositions containing the above-described surfactants, as well as methods of treating contact lenses with these surfactants. The compositions of the present invention may take various forms, depending on the intended uses of the compositions. Generally, the compositions of the present invention will find utility in previously known types of compositions for treating contact lenses which include one or more surfactants to facilitate cleaning or wetting of the lenses. The compositions will typically be aqueous solutions containing one or more polyalkylene oxide modified siloxanes in an amount sufficient to clean and wet the contact lenses being treated.

DETAILED DESCRIPTION OF THE INVENTION

The polyalkylene oxide modified siloxanes utilized in the present invention have an average molecular weight of less than 700 daltons. Preferred compounds have a molecular weight of approximately 550 to 650 daltons and a non-siloxane weight percent of approximately 65% to 80%. Most preferred is a compound known as PS071, which is commercially available from Hüls America, Inc., Piscataway, New Jersey. Product Number PS071 is described in the monograph "Silicon Compounds: Register and Review," 5th edition, R. Anderson, G.L. Larson and C. Smith, Editors, H üls America, Inc., Piscataway, New Jersey, 1991, page 276. PS071 is characterized by the following properties:

viscosity 20 cSt; refractive index 1.4416, specific gravity 1.007, melting point 0° C., surface tension 23.6 dynes/cm.

The preferred polyalkylene oxide modified siloxanes have the following formula:

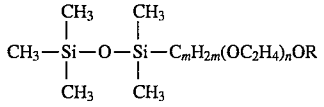

wherein m has a value from 2 to 4 inclusive, n has an average value from about 6 to 10 inclusive, and R is an alkyl group containing from 1 to 4 carbon atoms, such that the weight percent of the non-siloxane component (i.e., $(C_mH_{2m}(OC_2H_4)_nOR)$ is approximately 75% of the total average molecular weight and such average molecular weight is approximately 600 daltons.

The most preferred compound, PS071, is represented by the structural formula above, wherein m=3, n=approximately 8–10 and R is a methyl group.

Compounds with comparable molecular constitution and physicochemical properties include a surfactant known as Silwet L77, which is commercially available from Union Carbide Corporation, Danbury, Connecticut, and described in the product information brochure "Silwet Surface Active Copolymers," Union Carbide Corporation, 1985, and related product information sheets (Union Carbide Corporation, 1987).

The amount of polyalkylene oxide modified siloxane utilized will depend on various factors, such as the type of composition in which the copolymer is contained and the function of the composition. For example, compositions designed for out-of-the-eye cleaning of contact lenses by means of soaking the lenses in the composition will typically contain a higher concentration of copolymer than a composition designed for wetting of contact lenses by means of instilling a small amount of the composition directly on the lenses while in the eye. The concentration of copolymer may also depend on other factors, such as the type of contact lenses being treated (e.g., "hard" or "soft") and the presence of other ingredients in the formulation. Those skilled in the art will appreciate that the amount of copolymer utilized will depend on these and possibly other factors. For purposes of the present specification, the amounts required to clean or wet are functionally referred to as, "an effective amount". Such amounts will typically be in the range of about 0.0001 percent by weight (wt. %) to about 0.5 wt. % for wetting compositions, and about 0.01 wt. % to about 1.0 wt. % for cleaning compositions.

The compositions of the present invention may contain one or more of the above-described surfactants. The compositions may take various forms. For example, the compositions may be formulated as aqueous solutions, or solid or semi-solid preparations, such as tablets or gels. The surfactants utilized in the present invention may also be utilized in combination with other components for cleaning contact lenses, such as other siloxane or nonsiloxane surfactants, enzymes or deposit-shearing particles (e.g., microscopic beads formed from organic polymers).

The combined use of the above-described surfactants and one or more antimicrobial agents to clean and disinfect contact lenses by means of treatment with a single composition is another embodiment of the invention of particular interest. In this embodiment, the cleaning and disinfecting functions are combined into a single product: this simplifies the lens care regimen for contact lens wearers and generally makes the regimen more convenient. Examples of antimicrobial agents which may be combined with the above-described surfactants for this purpose include Polyquad® germicide (described below), benzalkonium chloride, chlorhexidine, polyaminopropyl biguanide and sorbic acid.

The lens cleaning compositions of this invention may also include conventional formulation ingredients, such as preservatives, viscosity enhancing agents, tonicity agents, and buffers. A polymeric quaternary ammonium germicide known as "POLYQUAD"® is a preferred preservative. The use of this germicide in contact lens care products is described in U.S. Pat. Nos. 4,407,791 and 4,525,346. Sorbic acid, which is also frequently utilized in contact lens care products, represents another preferred preservative. However, preservation of product can be achieved without the use of a conventional preservative. Such products may contain anionic, cationic and amphoteric surfactants in combination with polyalkylene oxide modified siloxanes. Solvents like propylene glycol or isopropyl alcohol, when added in sufficient amounts, can also eliminate the need for a conventional preservative. Viscosity enhancing agents which may be employed in the present invention include, for example, hydroxypropyl methylcellulose (HPMC) and dextrans. The tonicity agents, if employed, will typically comprise sodium chloride, potassium chloride, or a mixture thereof. The buffering agents may comprise, for example, boric acid, citric acid, phosphoric acid and pharmaceutically acceptable salts thereof with pharmacologically acceptable cations. The pH of the compositions may be adjusted using sodium hydroxide and hydrochloric acid; the present compositions preferably have a pH in the range of about 6.5 to about 7.8, and a tonicity in the range of about 200 mOsm/Kg to about 400 mOsm/Kg. The selection of particular formulation ingredients and the inclusion of these ingredients in the present compositions are well within the abilities of a person skilled in the art of contact lens care products. Thus, embodiments of the present invention may function as "all purpose solutions" for contact lens care, capable of simultaneously cleaning, wetting, disinfecting and conditioning the lens either out of the eye or while being worn.

The present invention also provides methods of cleaning and wetting contact lenses. The methods comprise contacting the lenses with the compositions for a time sufficient to achieve the desired objective, namely cleaning and/or wetting of the lenses. Various methods of contacting the lenses with the compositions may be utilized, depending on the type of composition utilized and the purpose of the treatment. For example, soiled lenses can be soaked in an aqueous solution containing one or more of the present compositions at room temperature in order to clean the lenses. If the lenses are excessively soiled or if it is desired to accelerate cleaning, heat or agitation (e.g., shaking or ultrasonic energy) can be applied to the vessel containing the solution. The lenses can also be cleaned by means of rubbing a small amount of a composition over the surfaces of the lenses. Such cleaning of the lenses also results in wetting of the lenses. Lenses can be wetted by soaking in a small volume of the composition for four to eight hours, for example. In addition, the lenses can be wetted by simply placing a small amount (e.g., one or two drops) of a composition directly on the lenses and placing the lenses on the eye. The instillation of a small amount of a composition on the lenses while being worn on the eye is also contemplated as a part of the present invention. Such instillation would effect both a cleansing and wetting of the lens in the eye.

The following examples are presented to further illustrate the present invention, but should not be interpreted as limiting the scope of the invention in any way.

Example 1

RGP Daily Cleaner (Suspension Type)

| Component | % w/v |
|---|---|
| Nylon 11 | 2.50 |
| Dextran 70 | 6.9 |
| Sodium Borate | 0.25 |
| Boric Acid | 0.50 |
| Miranol 2MCA Modified | 0.50 |
| Surfactant PS071 | 0.15 |
| Propylene Glycol | 10.0 |
| Polyquad ® | 0.005 |
| Disodium Edetate | 0.10 |
| Mannitol | 1.20 |
| Sodium Hydroxide/Hydrochloric Acid | adjust pH |
| Purified Water | qs |

Procedure

Prepare and sterilize the following filtration assemblies:

(i) 0.22 μm hydrophilic type sterilizing grade filter and receiving vessel;

(ii) 0.22 μm nylon sterilizing grade filter and receiving vessel.

Sterilize sufficient purified water, sodium hydroxide and hydrochloric acid for use in the following procedure.

Add approximately 40% of the final volume of purified water to a calibrated autoclavable processing vessel equipped with a stir bar, hydrophobic vent and dip tube with outlet for packaging. Dissolve the Dextran 70 in the purified water with mixing. Add the Miranol 2MCA Modified and allow to disperse. Disperse the Nylon 11 with mixing. Sterilize this composition by heating to 121° C. and holding this temperature for 30 minutes. Cool to room temperature (Composition A).

To another vessel equipped with a stir bar add approximately 20% of the final volume of purified water. Dissolve the boric acid and mannitol in the latter with mixing and continue mixing for an additional 30 minutes. Dissolve the sodium borate and disodium edetate with mixing and then add the Polyquad® with mixing. Pass this solution through a 0.22 μm pre-sterilized hydrophilic-type filtration assembly into a sterile receiver (Composition B).

Add the propylene glycol to a vessel equipped with a stir bar, and disperse the PS07 1 surfactant in the latter with mixing (15 minutes). Pass this mixture through a 0.22 μm pre-sterilized nylon filtration assembly into a sterile receiver (Composition C).

Aseptically add Composition B and Composition C to Composition A, assuring complete addition by rinsing with sterile purified water, and mix thoroughly. Aseptically adjust the pH of the mixture with sterile purified water and mix for a minimum of 15 minutes to yield the above-specified RGP Daily Cleaner.

Example 2

Demonstration of Cleaning Efficacy of

RGP Daily Cleaner (Example 1)

RGP lenses were deposited with an artificial meibum (lipid mixture). The soiled lenses were placed in the baskets of a Kestral lens case along with 5 ml of the RGP Daily Cleaner and allowed to soak for various periods of time (e.g., 2 hours, 4 hours, 6 hours). The percent of deposit remaining at the end of each soak period was determined by image analysis technology:

| Soak Time Hours | % Deposit Remaining |
|---|---|
| 0 | 100 |
| 2 | 3 |
| 4 | 0 |
| 6 | 0 |

Example 3

RGP Daily Cleaner (Suspension Type)

| Component | % w/v |
|---|---|
| Nylon 11 | 10.0 |
| Sodium Phosphate | 0.67 |
| Sodium Biphosphate | 0.17 |
| Sodium Chloride | 0.52 |
| Surfactant PS071 | 0.10 |
| Tyloxapol | 0.10 |

-continued

| Component | % w/v |
|---|---|
| Hydroxypropyl Methylcellulose | 0.60 |
| Polyquad ® | 0.001 |
| Disodium Edetate | 0.10 |
| Sodium Hydroxide/Hydrochloric Acid | adjust pH |
| Purified Water | qs |

Procedure

The composition may be prepared in a manner similar to the procedure of Example 1.

Example 4

RGP Daily Cleaner (Solution Type)

| Component | % w/v |
|---|---|
| Surfactant PS071 | 0.1 |
| Tyloxapol | 0.1 |
| Sodium Phosphate | 0.67 |
| Sodium Biphosphate | 0.17 |
| Sodium Chloride | 0.52 |
| Hydroxypropyl Methylcellulose | 0.30 |
| Disodium Edetate | 0.10 |
| Polyquad ® | 0.001 |
| Sodium Hydroxide/Hydrochloric Acid | adjust pH |
| Purified Water | qs |

Procedure

In a labeled, calibrated container with about 90% of the purified water, add and dissolve the following with continuous stirring:

Disodium Edetate

Sodium Phosphate

Sodium Biphosphate

Sodium Chloride

Tyloxapol

Surfactant PS071

Hydroxypropyl Methylcellulose

Polyquad®

Adjust the pH of the composition to pH 7.0 and add purified water to volume. Sterilize a receiving container connected to a 0.22 μm filter assembly. Sterile filter the composition and fill the container.

Example 5

RGP Daily Cleaner (Suspension Type)

| Component | % w/v |
|---|---|
| Nylon 11 | 2.50 |
| Sodium Borate | 0.25 |
| Boric Acid | 0.50 |
| Miranol 2MCA Modified | 0.50 |
| Surfactant PS071 | 0.15 |
| Propylene Glycol | 15.00 |
| Disodium Edetate | 0.10 |
| Mannitol | 1.20 |
| Sodium Hydroxide/Hydrochloric Acid | Adjust pH |
| Purified Water | qs |

Procedure

The composition is prepared in a manner similar to the procedure of Example 1.

Example 6

RGP Wetting/Soaking Solution

| Component | % w/v |
|---|---|
| Polyvinyl Alcohol 78,000/88% | 0.75 |
| Hydroxyethylcellulose 15,000 | 0.38 |
| Boric Acid | 0.35 |
| Sodium Borate | 0.11 |
| Mannitol | 2.0 |
| Disodium Edetate | 0.1 |
| Potassium Chloride | 0.038 |
| Magnesium Chloride | 0.02 |
| Calcium Chloride | 0.0154 |
| Sodium Chloride | 0.09 |
| Dextrose | 0.092 |
| Surfactant PS071 | 0.05 |
| Pluronic P103 | 0.05 |
| Polyquad ® | 0.001 |
| Sodium Hydroxide/Hydrochloric Acid | adjust pH |
| Purified Water | qs |

Procedure

Sterilize a filtration assembly connected to a receiving vessel. In a calibrated, labeled aspirator with about 40% of the required purified water, add and disperse the PS071 surfactant, the Pluronic P103 and the polyvinyl alcohol. If required, heat to 80° C. to disperse the polyvinyl alcohol.

Add and disperse the hydroxyethylcellulose. Connect a filtration assembly and autoclave for 30 minutes at 121° C.

In another container with about 30% of the required purified water, add and dissolve the sodium borate. Add the mannitol and stir for at least 15 minutes and then add the boric acid and stir for at least 30 minutes. Finally, add and dissolve the following with continuous stirring:

Disodium Edetate

Potassium Chloride

Magnesium Chloride

Calcium Chloride

Sodium Chloride

Dextrose

Polyquad®

Ascertain the pH of the salt solution and adjust the pH to 6.5.

Sterile filter the salt solution into the solution containing the PS071 surfactant/Pluronic P 103/hydroxyethylcellulose/polyvinyl alcohol.

Adjust the pH to 7.4 and add sufficient purified water to volume.

Example 7

RGP Wetting/Soaking Solution

| Component | % w/v |
|---|---|
| Polyvinyl Alcohol 78,000/88% | 0.75 |
| Hydroxyethylcellulose 15,000 | 0.38 |
| Potassium Chloride | 0.038 |
| Magnesium Chloride | 0.02 |
| Calcium Chloride | 0.0154 |

-continued

| Component | % w/v |
|---|---|
| Sodium Chloride | 0.714 |
| Sodium Phosphate | 0.008 |
| Dextrose | 0.092 |
| Surfactant PS071 | 0.01 |
| Pluronic F127 | 0.01 |
| Disodium Edetate | 0.10 |
| Polyquad ® | 0.001 |
| Sodium Hydroxide/Hydrochloric Acid | adjust pH |
| Purified Water | qs |

Procedure

Sterilize a filtration assembly connected to a receiving vessel.

In a calibrated, labeled aspirator with about 40% of the required purified water, add and disperse the PS071 surfactant, the Pluronic F127 and the polyvinyl alcohol. If required, heat to 80° C. to disperse the polyvinyl alcohol.

Add and disperse the hydroxyethylcellulose. Connect a filtration assembly and autoclave for 30 minutes at 121° C.

In another container with about 30% of the required purified water, add and dissolve the following with continuous stirring:

Disodium Edetate
Potassium Chloride
Magnesium Chloride
Calcium Chloride
Sodium Chloride
Sodium Phosphate
Dextrose
Polyquad®

Ascertain the pH of the salt solution and adjust the pH to 6.5.

Sterile filter the salt solution into the solution containing the PS071 surfactant/Pluronic P103/hydroxyethylcellulose/polyvinyl alcohol.

Adjust the pH to 7.0 and add sufficient purified water to volume.

What is claimed is:

1. A method of cleaning a contact lens, which comprises applying to the lens a composition comprising a polyalkylene oxide modified siloxane having an average molecular weight of less than 700 daltons and a non-siloxane weight percent of from about 65 to about 80 percent, in an amount effective to clean and wet the lens.

2. A method according to claim 1, wherein the polyalkylene oxide modified siloxane has an average molecular weight from about 550 to about 650 daltons.

3. A method according to claim 1, wherein the average molecular weight is about 600 daltons and the non-siloxane weight percent is about 75 percent.

4. A method according to claim 1, wherein the polyalkylene oxide modified siloxane has the following formula:

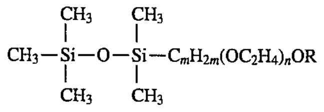

wherein m has a value from 2 to 4 inclusive, n has an average value from about 6 to 10 inclusive, and R is an alkyl group containing from 1 to 4 carbon atoms, such that the weight percent of the non-siloxane component is at least 65 percent of the total average molecular weight and such average molecular weight is from about 550 to about 650 daltons.

5. A method according to claim 4, wherein m=3, n has an average value from 8 to 10 inclusive, and R is a methyl group.

6. The method of claim 1, wherein the concentration of the polyalkylene oxide modified siloxane is from about 0.0001 weight percent to about 1.0 weight percent.

7. The method of claim 1, wherein the contact lens is a rigid gas permeable contact lens.

8. The method of claim 7, wherein the concentration of the polyalkylene oxide modified siloxane is from about 0.01 weight percent to about 0.5 weight percent.

9. The method of claim 1, wherein the contact lens is a soft contact lens.

10. The method of claim 1, wherein the composition is applied to the lens outside of the eye.

11. The method of claim 1, wherein the composition is applied to the lens while being worn.

12. A method of wetting a contact lens, which comprises applying to the lens a composition comprising a polyalkylene oxide modified siloxane having an average molecular weight of less than 700 daltons, in an amount effective to clean and wet the lens.

13. A method according to claim 12, wherein the polyalkylene oxide modified siloxane has an average molecular weight from about 550 to about 650 daltons.

14. A method according to claim 13, wherein the polyalkylene oxide modified siloxane has a non-siloxane weight percent of from about 65 to about 80 percent.

15. A method according to claim 14, wherein the average molecular weight is about 600 daltons and the non-siloxane weight percent is about 75 percent.

16. A method according to claim 12, wherein the polyalkylene oxide modified siloxane has the following formula:

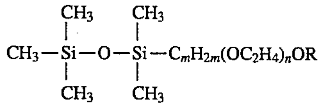

wherein m has a value from 2 to 4 inclusive, n has an average value from about 6 to 10 inclusive, and R is an alkyl group containing from 1 to 4 carbon atoms, such that the weight percent of the non-siloxane component is at least 65 percent of the total average molecular weight and such average molecular weight is from about 550 to about 650 daltons.

17. A method according to claim 16, wherein m=3, n has an average value from 8 to 10 inclusive, and R is a methyl group.

18. The method of claim 12, wherein the concentration of the polyalkylene oxide modified siloxane is from about 0.0001 weight percent to about 1.0 weight percent.

19. The method of claim 12, wherein the contact lens is a rigid gas permeable contact lens.

20. The method of claim 12, wherein the composition is applied to the lens outside of the eye.

21. The method of claim 12, wherein the composition is applied to the lens while being worn.

* * * * *